(12) United States Patent
Holly et al.

(10) Patent No.: US 9,277,943 B2
(45) Date of Patent: Mar. 8, 2016

(54) SURGICAL IMPLANT SYSTEM AND METHOD

(71) Applicant: Warsaw Orthopedic, Inc., Warsaw, IN (US)

(72) Inventors: Langston Holly, Encino, CA (US); Mark Dace, Collierville, TN (US); Kevin R. Humphreys, Oxford, MS (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 169 days.

(21) Appl. No.: 14/031,977

(22) Filed: Sep. 19, 2013

(65) Prior Publication Data

US 2015/0080969 A1 Mar. 19, 2015

(51) Int. Cl.
*A61B 17/70* (2006.01)
*A61B 17/80* (2006.01)

(52) U.S. Cl.
CPC ......... *A61B 17/7059* (2013.01); *A61B 17/8042* (2013.01)

(58) Field of Classification Search
CPC ... A61B 17/808; A61B 17/80; A61B 17/8019
See application file for complete search history.

(56) References Cited

U.S. PATENT DOCUMENTS

| | | | |
|---|---|---|---|
| 5,951,557 A | * | 9/1999 | Luter .......................... 606/286 |
| 2003/0060828 A1 | * | 3/2003 | Michelson .................... 606/71 |
| 2007/0123884 A1 | * | 5/2007 | Abdou ........................ 606/69 |
| 2010/0262193 A1 | * | 10/2010 | Frigg et al. ................... 606/281 |

* cited by examiner

*Primary Examiner* — Andrew Yang

(57) ABSTRACT

A spinal implant comprises a wall extending between a first end and a second end and defining a longitudinal axis. The wall has a first surface and a second surface configured to engage tissue. The wall defines at least one opening configured for disposal of a bone fastener. The first end includes an inner surface comprising a first linear side and a second linear side. The linear sides are disposed in substantial alignment with the axis. The inner surface further comprises an arcuate side connected to the linear sides to define a cavity configured for disposal of a fastener. Systems and methods are disclosed.

19 Claims, 5 Drawing Sheets

SURGICAL IMPLANT SYSTEM AND METHOD

TECHNICAL FIELD

The present disclosure generally relates to medical devices for the treatment of musculoskeletal disorders, and more particularly to a surgical system for fastening implants to tissue at a surgical site and a method for treating a spine.

BACKGROUND

Spinal pathologies and disorders such as scoliosis and other curvature abnormalities, kyphosis, degenerative disc disease, disc herniation, osteoporosis, spondylolisthesis, stenosis, tumor, and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, discectomy, laminectomy, correction and implantable prosthetics. As part of these surgical treatments, implants such as bone fasteners, plates, connectors and vertebral rods are often used to provide stability to a treated region. These implants can redirect stresses away from a damaged or defective region while healing takes place to restore proper alignment and generally support the vertebral members. For example, rods and plates may be attached via the fasteners to the exterior of one or more vertebral members. This disclosure describes an improvement over these prior art technologies.

SUMMARY

In one embodiment, a spinal implant is provided. The spinal implant comprises a wall extending between a first end and a second end and defining a longitudinal axis. The wall has a first surface and a second surface configured to engage tissue. The wall defines at least one opening configured for disposal of a bone fastener. The first end includes an inner surface comprising a first linear side and a second linear side. The linear sides are disposed in substantial alignment with the axis. The inner surface further comprises an arcuate side connected to the linear sides to define a cavity configured for disposal of a fastener. In some embodiments, systems and methods are disclosed.

BRIEF DESCRIPTION OF THE DRAWINGS

The present disclosure will become more readily apparent from the specific description accompanied by the following drawings, in which.

DETAILED DESCRIPTION

Figure 1:
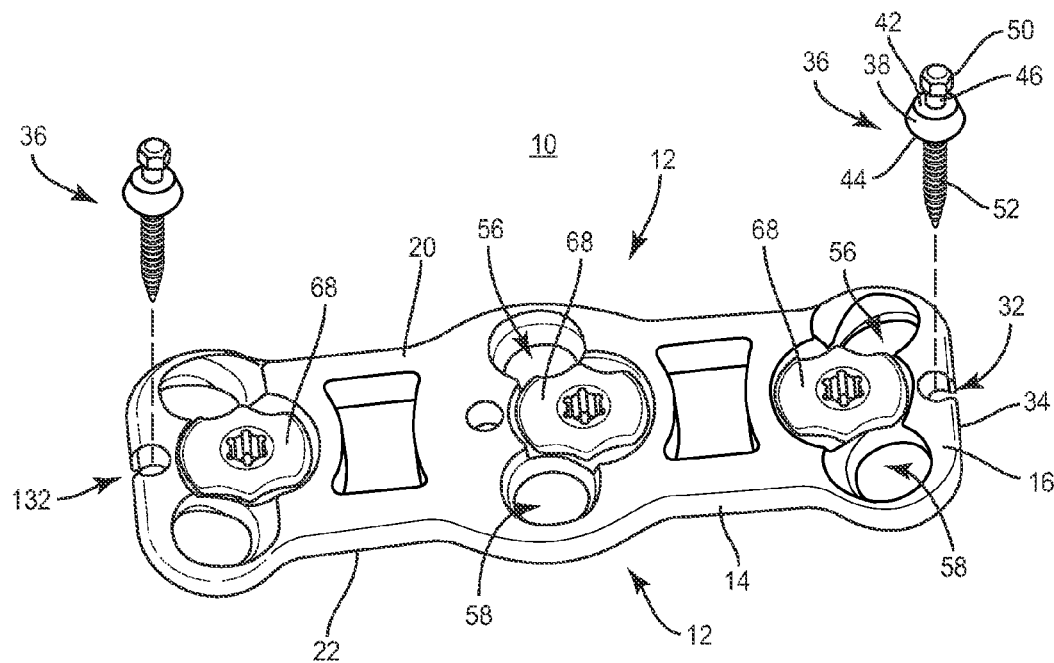
FIG. 1 is a perspective view of components of one embodiment of a surgical system in accordance with the principles of the present disclosure.

The exemplary embodiments of a surgical implant system are discussed in terms of medical devices for the treatment of musculoskeletal disorders and more particularly, in terms of a surgical implant system for delivering and/or fastening implants with a surgical site and a method for treating a spine.

In one embodiment, the surgical implant system includes a spinal plate having a partially open cavity at the ends of the plate. In one embodiment, the surgical implant system includes a spinal plate having a partial opening at the ends of the plate configured to allow a pre-fixation pin to pass through and the partial opening fully captures the pin. In one embodiment, the partial opening has an omega-shape. In one embodiment, the partial opening supports a fixation pin while avoiding lengthening of the plate to accommodate the fixation pin. In one embodiment, the partial opening provides a space such that the spinal plate avoids interference with spinal constructs, such as, for example, distraction pins.

In some embodiments, the surgical implant system of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the surgical implant system of the present disclosure may be employed with other osteal and bone related applications, including those associated with diagnostics and therapeutics. In some embodiments, the disclosed surgical implant system may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions. The surgical implant system of the present disclosure may also be alternatively employed with procedures for treating the lumbar, cervical, thoracic, sacral and pelvic regions of a spinal column. The surgical implant system of the present disclosure may also be used on animals, bone models and other non-living substrates, such as, for example, in training, testing and demonstration.

The surgical implant system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

Figure 2:
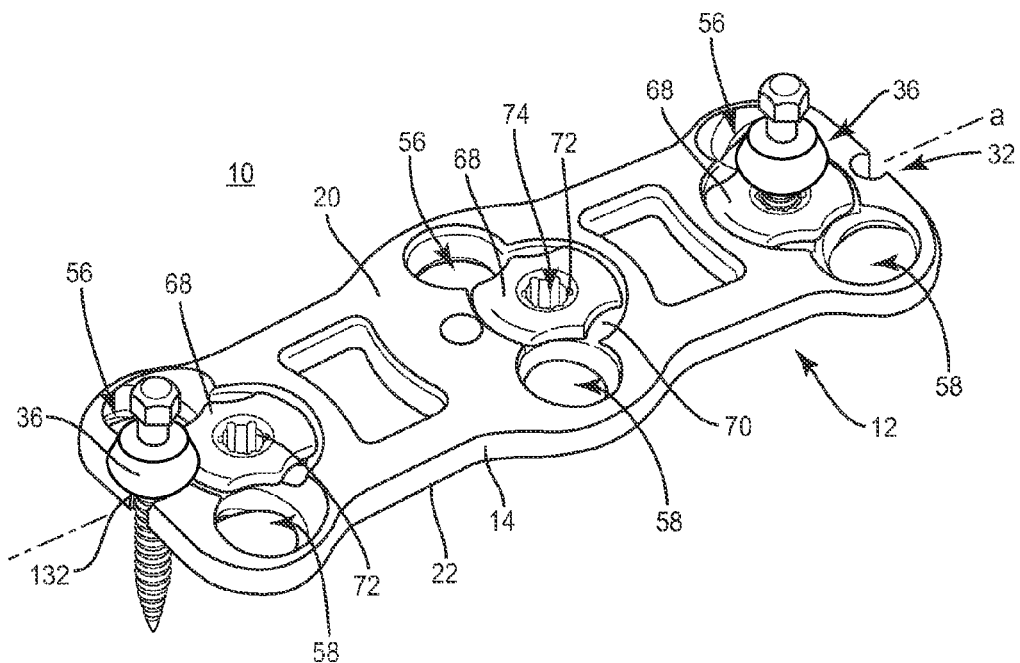
FIG. 2 is a perspective view of the components shown in FIG. 1.
Figure 3:
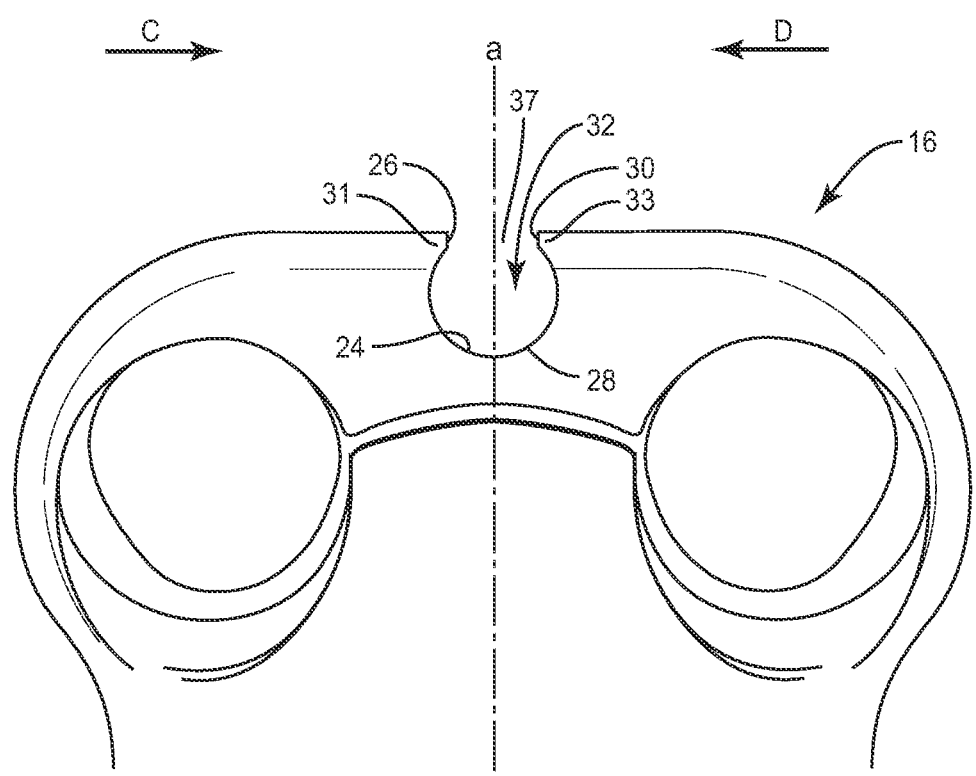
FIG. 3 is an enlarged break away view a component shown in FIG. 1.

The following discussion includes a description of a surgical implant system, related components and methods of employing the surgical implant system in accordance with the principles of the present disclosure. Alternate embodiments are also disclosed. Reference will now be made in detail to the exemplary embodiments of the present disclosure, which are illustrated in the accompanying figures. Turning to FIGS. 1-3, there are illustrated components of a surgical implant system 10.

The components of surgical implant system 10 can be fabricated from biologically acceptable materials suitable for medical applications, including metals, synthetic polymers, ceramics and bone material and/or their composites, depending on the particular application and/or preference of a medical practitioner. For example, the components of surgical implant system 10, individually or collectively, can be fabricated from materials such as stainless steel alloys, commercially pure titanium, titanium alloys, Grade 5 titanium, superelastic titanium alloys, cobalt-chrome alloys, stainless steel alloys, superelastic metallic alloys (e.g., Nitinol, super elastoplastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of surgical implant system 10 may have material composites, including the above materials, to achieve various desired characteristics such as strength, rigidity, elasticity, compliance, biomechanical performance, durability and radiolucency or imaging preference. The components of surgical implant system 10, individually or collectively, may also be fabricated from a heterogeneous material such as a combination of two or more of the above-described materials. The components of surgical implant system 10 may be monolithically formed, integrally connected or include fastening elements and/or instruments, as described herein.

Surgical implant system 10 is employed, for example, with an open or mini-open, minimal access and/or minimally invasive including percutaneous surgical technique to deliver and fasten an implant, such as, for example, an anterior cervical plate at a surgical site within a body of a patient, for example, a section of a spine. In one embodiment, the components of surgical implant system 10 are configured to temporarily fix an implantable plate with a provisional fastener to selectively position and orient the plate relative to tissue for a surgical treatment to treat various spine pathologies, such as those described herein. In one embodiment, upon selected positioning and orientation of the plate, permanent fixation elements of system 10 are employed to fix the plate with tissue and the provisional fastener is removed from the tissue. In some embodiments, the provisional fastener can be removed from tissue before or after fixation of the permanent fixation elements. In one embodiment, a permanent fixation element includes components implanted with tissue and remaining after a surgical procedure is completed and an incision is closed. In one embodiment, a permanent fixation element includes components implanted with tissue and remaining after a first and/or initial surgical procedure is completed and an incision is closed, and the component is removable in a second, subsequent and/or separate surgical procedure.

Surgical implant system 10 includes a spinal implant, such as, for example, an anterior cervical plate 12. In some embodiments, plate 12 is configured for connecting three vertebral bodies, each vertebral body receiving two fasteners, one fastener through each opening. Plate 12 has a substantially rectangular shape and a continuous lordotic curve along its length to accommodate the curvature of the spinal column. In some embodiments, plate 12 is variously shaped, such as, for example, oval, oblong, triangular, polygonal, irregular, uniform, non-uniform, variable and/or tapered.

Figure 4:
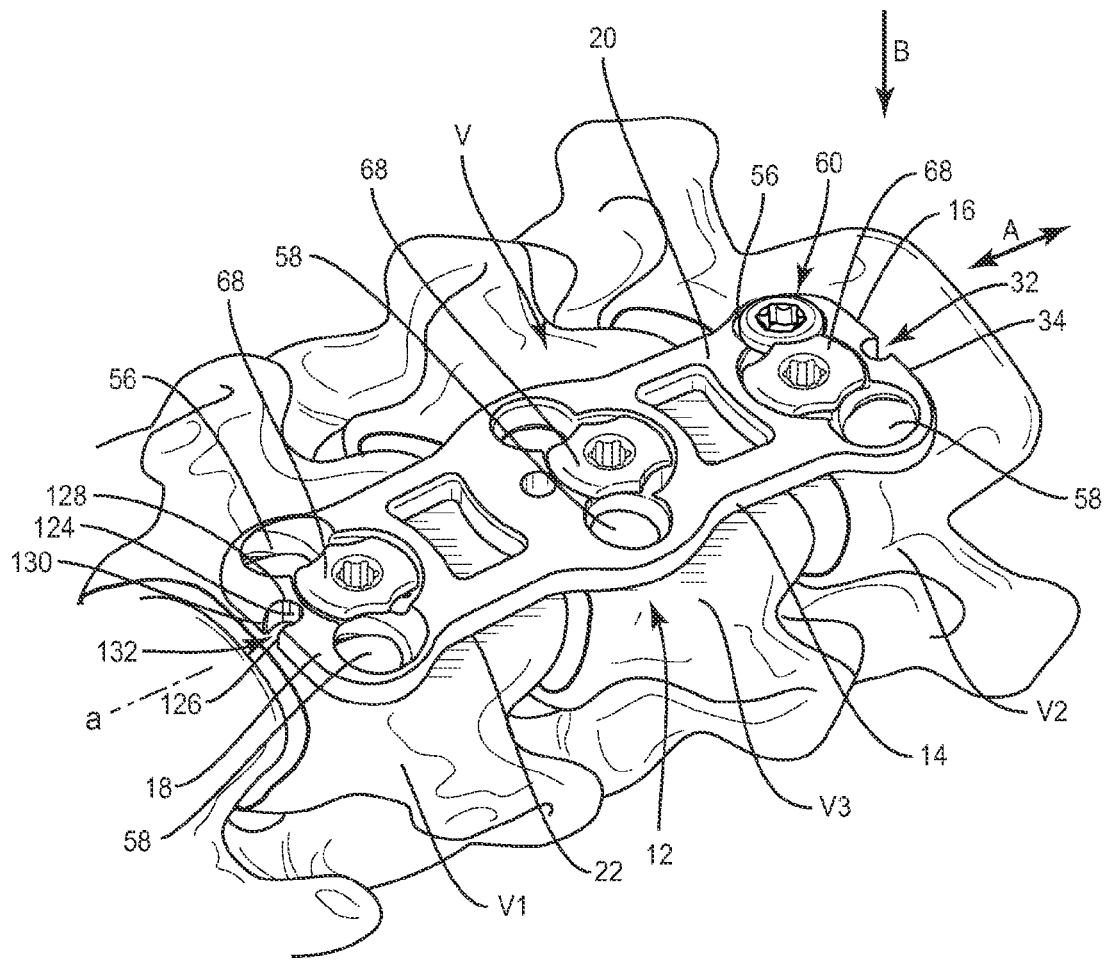
FIG. 4 is a perspective view of components of one embodiment of a surgical system in accordance with the principles of the present disclosure disposed with vertebrae.

Plate 12 is elongated such that when plate 12 is disposed with vertebrae, plate 12 extends between a midpoint of a vertebral body V1 and a midpoint of a vertebral body V2, as shown in FIG. 4. Vertebral bodies V1, V2 are disposed adjacent a vertebral body V3. A midpoint along a length of plate 12 is centrally disposed with vertebral body V3.

Plate 12 includes a wall 14 extending between an end 16 and an end 18. Wall 14 defines a longitudinal axis a. Wall 14 has a surface 20 configured for orientation in an anterior direction of a body and a surface 22 configured for orientation in a posterior direction to engage an anterior portion of vertebrae V. In some embodiments, surface 20 and/or surface 22 may have various surface configurations, such as, for example, rough, threaded, arcuate, undulating, porous, semi-porous, dimpled, polished and/or textured.

End 16 includes an inner surface 24 comprising a linear side 26 and a linear side 30, as shown in FIG. 3. Linear sides 26, 30 are disposed in substantially parallel alignment with axis a. Inner surface 24 comprises an arcuate side 28 connected to linear sides 26, 30 to define a cavity 32 configured for disposal of a provisional fastener, such as, for example, a pre-fixation pin 36, described herein. In some embodiments, linear sides 26, 30 may be disposed in various alternative orientations relative to axis a, such as, for example, relative angular orientations including acute or obtuse, offset and/or staggered and/or may be oriented in various planes of a body, such as, for example, coronal, sagittal and/or transverse. In some embodiments, linear sides 26, 30 may be disposed in various alternative orientations relative to arcuate side 28, such as, for example, those described herein. In some embodiments, arcuate side 28 may include linear portion and/or have alternate radii portions.

End 16 includes an edge surface 34 having an opening 37 that communicates with cavity 32 to facilitate passage of pin 36 into and out of cavity 32 in an axial orientation, as shown by arrows A in FIG. 4, relative to axis a. In some embodiments, cavity 32 is configured for receiving pin 36 in a lateral orientation that is transverse to axis a, as shown by arrow B in FIG. 4, and an axial orientation, as shown by arrows A in FIG. 4, relative to the axis a. Cavity 32 and opening 37 are disposed in an omega-shape cross-section configuration. Cavity 32 and opening 37 extend completely through surfaces 20, 22.

Cavity 32 and opening 37 are centrally disposed along end 16 and edge surface 34. Edge surface 34 includes flanges 31, 33 that extend to linear sides 26, 30, respectively, such that end 16 captures pin 36 for temporary fixation in a selected orientation with vertebrae V. Linear side 26 defines a planar face oriented in a first direction, as shown by arrow C in FIG. 3, and linear side 30 defines a planar face oriented in a second opposing direction, as shown by arrow D in FIG. 3.

End 18 includes an inner surface 124, as shown in FIG. 4, comprising a linear side 126 and a linear side 130, disposed in substantially parallel alignment with axis a, and comprising an arcuate side 128, similar to the components of end 16 described herein. Arcuate side 128 is connected to linear sides 126, 130 to define a cavity 132 configured for disposal of a pre-fixation pin 36, described herein.

Pre-fixation pin 36 is provisionally disposed with cavity 32 and/or cavity 132 and tissue, such as, for example, vertebrae V to selectively position and orient plate 12 relative to vertebrae V. Flanges 31, 33 and/or the flanges of end 18 are sized and shaped such that a shaft 52 of pin 36 is captured with cavity 32 and/or the cavity of end 18 of plate 12.

Pin 36 includes a head 38. Head 38 includes a surface 42 and a surface 44. In some embodiments, surfaces 42, 44 may have surface configurations to enhance engagement, such as, for example, rough, arcuate, undulating, dimpled and/or textured. In some embodiments, all or only a portion of head 38 may have cross section configurations, such as, for example, oval, oblong, triangular, square, polygonal, irregular, uniform, non-uniform, offset, staggered, and/or tapered. For example, surface 44 is configured to overlap at least a portion of cavity 32 and surface 42 to provisionally retain and stabilize plate 12 for positioning and orientation of plate 12, as discussed herein.

Head 38 includes a stem 46 extending along an axis of pin 36 from surface 42 of head 38. Stem 46 includes a drive interface 50. Drive interface 50 is configured for engagement with a tool, such as, for example a driver. Drive interface 50 is spaced apart from surface 42 by a length of stem 46. In some embodiments, interface 50 can be alternatively configured, such as, for example, a tri-flat shape having three planar surfaces arranged about an axis of interface 50, square, hexagonal, polygonal, star, groove, Phillips, cruciate, slot or hexalobe cross sectional configuration. In some embodiments, all or only a portion of head 38 may have cross section configurations, such as, for example, hexagonal, oval, oblong, triangular, square, polygonal, irregular, uniform, non-uniform, offset, staggered, and/or tapered.

Pin 36 includes a penetrating element, such as, for example, a threaded shaft 52. Shaft 52 is configured for disposal in cavity 32. In some embodiments, pin 36 may include one or a plurality of penetrating elements. Shaft 52 extends axially from head 38 in a direction opposite to stem 46. In some embodiments, the penetrating elements can include, such as, for example, barbs, nails or pins. Shaft 52 penetrates tissue including bone for temporary and/or provisional fixation.

Plate 12 defines a series of paired openings, such as, for example, openings 56, 58 extending through surfaces 20, 22. Openings 56, 58 are configured for disposal of permanent implantable fixation elements, such as, for example, bone screws 60 for permanently attaching plate 12 with tissue.

Bone screw 60 comprises a head and an elongated shaft configured for penetrating tissue. In some embodiments, surgical implant system 10 may include one or a plurality of fixation elements. The shaft of bone screw 60 has a cylindrical cross section configuration and includes an outer surface having an external threaded form (not shown). In some embodiments, the thread form may include a single thread turn or a plurality of discrete threads. In some embodiments, other engaging structures may be located on the shaft of bone screw 60, such as, for example, a nail configuration, barbs, expanding elements, raised elements and/or spikes to facilitate engagement of shaft 64 with tissue, such as, for example, vertebrae.

In some embodiments, all or only a portion of the shaft of bone screw 60 may have alternate cross section configurations, such as, for example, oval, oblong, triangular, square, polygonal, irregular, uniform, non-uniform, offset, staggered, undulating, arcuate, variable and/or tapered. In some embodiments, the outer surface of the shaft of bone screw 60 may include one or a plurality of openings. In some embodiments, all or only a portion of the outer surface of the shaft of bone screw 60 may have alternate surface configurations to enhance fixation with tissue such as, for example, rough, arcuate, undulating, mesh, porous, semi-porous, dimpled and/or textured according to the requirements of a particular application. In some embodiments, all or only a portion of the shaft of bone screw 60 may be disposed at alternate orientations, relative to its longitudinal axis, such as, for example, transverse, perpendicular and/or other angular orientations such as acute or obtuse, co-axial and/or may be offset or staggered. In some embodiments, all or only a portion of the shaft of bone screw 60 may be cannulated.

Plate 12 includes retaining elements 68 disposed between openings 56, 58 so as to resist and/or prevent inadvertent back out of bone screws 60 after bone screws 60 have been fully inserted into openings 56, 58. Plate 12 includes a recess 70 in surface 20 dimensioned to correspond to retaining element 68. Retaining element 68 is configured to engage recess 70 such that retaining element 68 is rotatable between a locking orientation and a non-locking orientation. In the locking orientation, retaining element 68 resists and/or prevents backout of bone screws 60 from openings 56, 58. In the non-locking orientation, bone screws 60 are axially translatable through openings 56, 58. Plate 12 includes three retaining elements 68 each being disposed between each pair of openings 56, 58 in plate 12.

Retaining element 68 includes an inner surface 72 that defines a centrally disposed aperture 74 extending through surfaces 20, 22 of plate 12. Aperture 74 is configured for disposal of shaft 52. Inner surface 72 has a hexagonal configuration configured to engage a correspondingly shaped portion of a driving tool (not shown) for rotating retaining element 68 with respect to recess 70 between the locking and non-locking orientations. In some embodiments, inner surface 72 may be variously configured to engage, such as, for example, a Phillips head, slotted head, hex socket head, hexagon external head, frearson head, square socket, square slotted combination head, spanner drilled tamper proof head and combinations thereof.

In assembly, operation and use, an implant system, similar to surgical implant system 10 described herein, is employed with a surgical procedure for treatment of a spinal disorder affecting a section of a spine of a patient, as discussed herein. For example, surgical implant system 10 can be used with a surgical procedure for treatment of a condition or injury of an affected section of the spine including vertebrae. In some embodiments, one or all of the components of surgical implant system 10 can be delivered or implanted as a pre-assembled device or can be assembled in situ. Surgical implant system 10 may be completely or partially revised, removed or replaced.

For example, surgical implant system 10 can be employed with a surgical treatment of an applicable condition or injury of an affected section of a spinal column and adjacent areas within a body, such as, for example, cervical vertebrae V, as shown in FIG. 4. In some embodiments, surgical implant system 10 may be employed with one or a plurality of vertebra. To treat a selected section of vertebrae V, a medical practitioner obtains access to a surgical site including vertebrae V in any appropriate manner, such as through incision and retraction of tissues. In some embodiments, surgical implant system 10 can be used in any existing surgical method or technique including open surgery, mini-open surgery, minimally invasive surgery and percutaneous surgical implantation, whereby vertebrae V are accessed through a mini-incision, or sleeve that provides a protected passageway to the area. Once access to the surgical site is obtained, the particular surgical procedure can be performed for treating the spine disorder.

An incision is made in the body of a patient and a cutting instrument (not shown) creates a surgical pathway for implantation of components of surgical implant system 10. A preparation instrument (not shown) can be employed to prepare tissue surfaces of vertebrae V, as well as for aspiration and irrigation of a surgical region according to the requirements of a particular surgical application.

Plate 12 is delivered to the surgical site adjacent vertebrae V and over distraction pins (not shown). Plate 12 is disposed in a selected position and orientation relative to vertebrae V such that surface 22 of plate 12 is disposed with tissue and aperture 74 is disposed approximately at the mid-portion of vertebral body V3. Pins 36 are positioned in at least one of cavity 32 in end 16, cavity 132 in end 18, and one or more apertures 74 in retaining elements 68 to temporarily fix plate 12 with vertebrae V in a selected position and orientation.

A tool (not shown) is utilized to engage drive interface 50 and drive pin 36 into engagement with surface 20 of plate 12 and penetration with vertebrae V. Shaft 52 passes through cavity 32 of plate 12 and penetrates tissue including bone of vertebrae V. Pin 36 is captured, for example, within cavity 32 by flanges 31, 33 to temporarily and/or provisionally fix and retain plate 12 with cavity 32 and vertebrae V to selectively position and orient plate 12 relative to vertebrae V.

Pilot holes or the like are made in selected vertebra of vertebrae V corresponding to openings 56, 58 for receiving fixation elements, such as, for example, bone screws 60. Bone screws 60 are disposed adjacent vertebrae V at a surgical site and the components of surgical implant system 10 including a driver, are manipulable to drive, torque, insert or otherwise connect bone screws 60 with vertebrae V for fastening plate 12 with vertebrae V, according to the particular requirements of the surgical treatment. Bone screws 60 are fully inserted and permanently implanted through openings 56, 58 of plate 12 with tissue to permanently implant plate 12 in the selected position and orientation. Pins 36 are removed from cavities 32, 132 and tissue. A driving tool (not shown) is positioned within aperture 74 to rotate retaining element 68 from the non-locking orientation to the locking orientation such that retaining element 68 partially overlaps bone screws 60 and openings 56, 58 to resist and/or prevent inadvertent back out of bone screws 60 from plate 12 and/or tissue.

Upon completion of the procedure, the surgical instruments, assemblies and non-implanted components of surgical implant system 10 are removed from the surgical site and the incision is closed. Surgical implant system 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of surgical implant surgical implant system 10.

In some embodiments, surgical implant system 10 may include one or a plurality of plates, connectors, spinal rods and/or bone fasteners for use with a single vertebral level or a plurality of vertebral levels. In some embodiments, the plates, connectors, spinal rods and/or bone fasteners may be engaged with vertebrae in various orientations, such as, for example, series, parallel, offset, staggered and/or alternate vertebral levels. In some embodiments, the bone fasteners may include one or a plurality of multi-axial screws, sagittal angulation screws, pedicle screws, mono-axial screws, uni-planar screws, fixed screws, tissue penetrating screws, conventional screws, expanding screws, anchors, buttons, connectors, clips, snaps, friction fittings, compressive fittings, expanding rivets, staples, nails, adhesives, fixation plates and/or posts. The plates, connectors, spinal rods and/or bone fasteners may be coated with an osteoinductive or osteoconductive material to enhance fixation, and/or include one or a plurality of therapeutic agents.

In one embodiment, surgical implant system 10 includes an agent, which may be disposed, packed, coated or layered within, on or about the components and/or surfaces of surgical implant system 10. In some embodiments, the agent may include bone growth promoting material, such as, for example, bone graft to enhance fixation of the fixation elements with vertebrae. In some embodiments, the agent may include one or a plurality of therapeutic agents and/or pharmacological agents for release, including sustained release, to treat, for example, pain, inflammation and degeneration.

Figure 5:
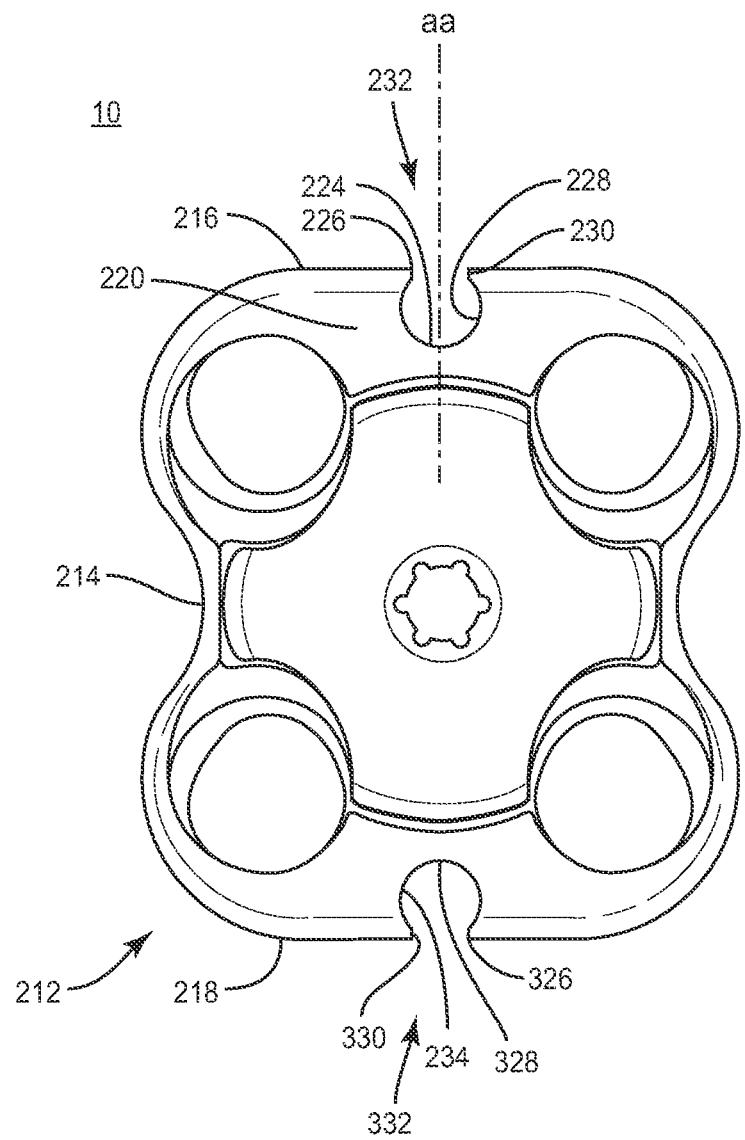
FIG. 5 is a perspective view of components of one embodiment of a surgical system in accordance with the principles of the present disclosure.
Figure 6:
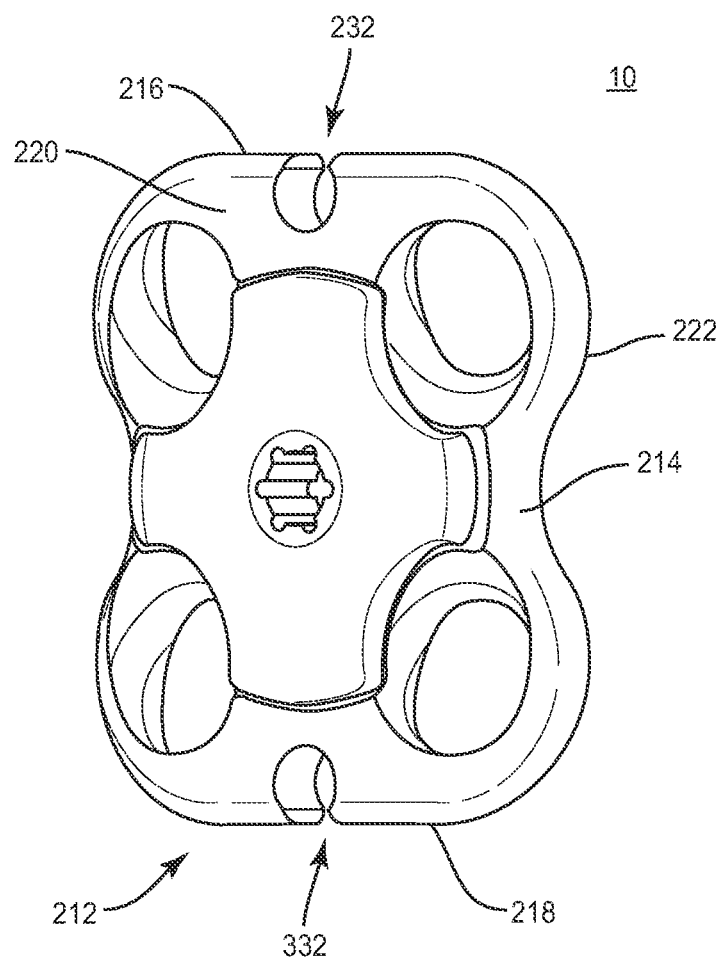
FIG. 6 is a perspective view of the components shown in FIG. 5.

In one embodiment, as shown in FIGS. 5 and 6, surgical implant system 10, similar to the systems and methods described above with regard to FIGS. 1-4, includes a plate 212, similar to plate 12 described herein. In some embodiments, plate 212 is configured for connecting three vertebral bodies, each vertebral body receiving two fasteners, one fastener through each opening. Plate 212 has a substantially square configuration.

Plate 212 includes a wall 214 extending between an end 216 and an end 218. Wall 214 defines a longitudinal axis aa. Wall 214 has a surface 220 configured for orientation in an anterior direction of a body and a surface 222 configured for orientation in a posterior direction to engage an anterior portion of vertebrae V.

End 216 includes an inner surface 224 comprising a linear side 226 and a linear side 230, disposed in substantially parallel alignment with axis aa, and comprising an arcuate side 228, similar to the components of end 16 described herein. Arcuate side 228 is connected to linear sides 226, 230 to define a cavity 232 configured for disposal of a pre-fixation pin 36, described herein.

End 218 includes an inner surface 234 comprising a linear side 326 and a linear side 330, disposed in substantially parallel alignment with axis aa, and comprising an arcuate side 328, similar to the components of end 16 described herein. Arcuate side 328 is connected to linear sides 326, 330 to define a cavity 332 configured for disposal of a pre-fixation pin 36, described herein.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal implant comprising:
   a fastener;
   a wall extending between a first end and a second end and defining a longitudinal axis, the wall having a first surface and a second surface configured to engage tissue,
   the wall defining at least one opening configured for disposal of a bone fastener,
   the first end includes an inner surface comprising a first linear side and a second linear side, the linear sides being disposed in substantial alignment with the axis, the inner surface further comprising an arcuate side connected to the linear sides to define a cavity configured for disposal of the fastener, each of the linear sides including a flange, the fastener comprising a threaded shaft that engages the flanges and the arcuate side to capture the fastener; and
   a retaining element configured to resist and/or prevent inadvertent back out of the bone fastener from the at least one opening.

2. A spinal implant as recited in claim 1, wherein the cavity is configured for receiving the fastener in a lateral orientation and an axial orientation, relative to the axis.

3. A spinal implant as recited in claim 1, wherein the cavity is configured for passage of the fastener into and out of the cavity in an axial orientation, relative to the axis.

4. A spinal implant as recited in claim 1, wherein the first linear side defines a planar face oriented in a first direction and the second linear side defines a planar face oriented in a second opposing direction.

5. A spinal implant as recited in claim 1, wherein the first end includes an edge surface and the linear sides define an opening of the edge surface.

6. A spinal implant as recited in claim 5, wherein the opening of the edge surface is centrally disposed along the edge surface.

7. A spinal implant as recited in claim 5, the opening of the edge surface facilitates passage of the fastener into and out of the cavity in an axial orientation, relative to the axis.

8. A spinal implant as recited in claim 1, wherein the wall comprises a cervical plate.

9. A spinal implant as recited in claim 1, wherein the cavity includes an omega-shaped cross section.

10. A spinal implant as recited in claim 1, wherein the cavity extends completely through the first surface and the second surface.

11. A spinal implant as recited in claim 1, wherein the retaining element is rotatable between a locking orientation to resist and/or prevent inadvertent back out of the bone fastener from the at least one opening and a non-locking orientation such that the bone fastener is translatable transverse to the axis through the at least one opening.

12. A spinal implant as recited in claim 1, further comprising a second fastener extending through an aperture in the retaining element, the second fastener comprising a threaded shaft configured to penetrate bone.

13. A spinal implant as recited in claim 1, further comprising a second fastener having a threaded shaft, wherein the retaining element includes an inner surface that defines a centrally disposed aperture and holes at opposite ends that are in communication with the aperture, the second fastener being positioned within the aperture such that the threaded shaft extends through the holes.

14. A spinal implant as recited in claim 1, wherein the at least one opening comprises a pair of openings, central portions of the openings each being intersected a lateral axis that extends perpendicular to the longitudinal axis, the cavity being spaced apart from the lateral axis.

15. A spinal implant as recited in claim 1, wherein the second end includes an inner surface comprising a first linear side and a second linear side, the linear sides of the second end being disposed in substantial alignment with the axis, the inner surface of the second end further comprising an arcuate side connected to the linear sides of the second end to define a cavity, each of the linear sides of the second end including a flange, the flanges of the second end being configured to capture a second fastener within the cavity of the second end.

16. A spinal implant comprising:
   a provisional fastener;
   a plate extending between a first end and a second end, the plate having a first surface configured for orientation in an anterior direction and a second surface configured for orientation in a posterior direction to engage an anterior portion of vertebrae, the plate defining a plurality of openings, each opening being configured for disposal of a bone fastener,
   the first end including an inner surface comprising a first linear side and a second linear side, the linear sides being disposed in substantial alignment with the axis, the inner surface further comprising an arcuate side connected to the linear sides to define a cavity configured for disposal of the provisional fastener, each of the linear sides including a flange, the provisional fastener comprising a threaded shaft that engages the flanges and the arcuate side to capture the provisional fastener, the first end further including an edge surface having an opening that communicates with the cavity to facilitate passage of a provisional fastener into and out of the cavity in an axial orientation, relative to the axis,
   the second end including an inner surface comprising a first linear side and a second linear side, the linear sides of the second end being disposed in substantial alignment with the axis, the inner surface of the second end further comprising an arcuate side connected to the linear sides of the second end to define a cavity configured for disposal of a provisional fastener, the second end further including an edge surface having an opening that communicates with the cavity of the second end to facilitate passage of a provisional fastener into and out of the cavity of the second end in an axial orientation, relative to the axis; and a retaining element configured to resist and/or prevent inadvertent back out of two of the bone fasteners from two of the plurality of openings.

17. A surgical implant system comprising:

a provisional fastener;

a wall extending between a first end and a second end and defining a longitudinal axis, the wall having a first surface and a second surface configured to engage tissue, the first end includes an inner surface comprising a first linear side and a second linear side, the linear sides being disposed in substantial alignment with the axis, the inner surface further comprising an arcuate side connected to the linear sides to define a cavity, each of the linear sides including a flange, the provisional fastener comprising a threaded shaft that engages the flanges and the arcuate side to capture the provisional fastener, the wall further defining a plurality of openings;

a plurality of bone fasteners, each bone fastener being configured for disposal with an opening of the plurality of openings; and a retaining element configured to resist and/or prevent inadvertent back out of at least one of the bone fasteners from at least one opening of the plurality of openings, wherein the cavity is configured for passage of the provisional fastener into and out of the cavity in an axial orientation, relative to the axis.

18. A spinal implant as recited in claim 17, wherein the cavity includes an omega-shaped cross section.

19. A spinal implant as recited in claim 17, wherein the first end includes an edge surface and the linear sides define an opening of the edge surface such that the opening of the edge surface facilitates passage of the provisional fastener into and out of the cavity in an axial orientation, relative to the axis.

* * * * *